(12) United States Patent
McGivney et al.

(10) Patent No.: US 9,159,537 B2
(45) Date of Patent: Oct. 13, 2015

(54) METHOD FOR ANALYZING SAMPLE COMPONENTS

(71) Applicants: MedImmune, LLC, Gaithersburg, MD (US); University of Notre Dame Du Lac, Notre Dame, IN (US)

(72) Inventors: James McGivney, Gaithersburg, MD (US); Guijie Zhu, Notre Dame, IN (US); Norman Dovichi, Notre Dame, IN (US)

(73) Assignees: University of Notre Dame du Lac, Notre Dame, IN (US); Medimmune, LLC, Gaithersburg, MD (US)

(*) Notice: Subject to any disclaimer, the term of this patent is extended or adjusted under 35 U.S.C. 154(b) by 0 days.

(21) Appl. No.: 14/395,862

(22) PCT Filed: May 2, 2013

(86) PCT No.: PCT/US2013/039286
§ 371 (c)(1),
(2) Date: Oct. 21, 2014

(87) PCT Pub. No.: WO2013/166297
PCT Pub. Date: Nov. 7, 2013

(65) Prior Publication Data
US 2015/0162177 A1 Jun. 11, 2015

Related U.S. Application Data

(60) Provisional application No. 61/641,975, filed on May 3, 2012.

(51) Int. Cl.
*C12Q 1/68* (2006.01)
*G01N 30/72* (2006.01)
*G01N 1/00* (2006.01)
*H01J 49/00* (2006.01)
*H01J 49/26* (2006.01)
*H01J 49/16* (2006.01)
*G01N 27/447* (2006.01)

(52) U.S. Cl.
CPC .......... *H01J 49/0031* (2013.01); *G01N 27/447* (2013.01); *H01J 49/165* (2013.01); *H01J 49/26* (2013.01)

(58) Field of Classification Search
USPC ........ 250/281–283, 288, 526; 435/4, 6.1, 7.1, 435/285.2, 286.5, 287.1, 287.9, 288.4, 435/288.5, 288.6; 436/514, 515, 516, 518; 422/63, 67, 68.1; 204/450, 451, 452, 204/459, 461
See application file for complete search history.

(56) References Cited

U.S. PATENT DOCUMENTS

| | | | |
|---|---|---|---|
| 5,164,055 A * | 11/1992 | Dubrow | 204/455 |
| 7,615,354 B2 * | 11/2009 | Faupel et al. | 435/7.1 |
| 8,932,830 B2 * | 1/2015 | Peters et al. | 435/69.7 |
| 2003/0104449 A1 * | 6/2003 | Faupel et al. | 435/6 |
| 2005/0032202 A1 * | 2/2005 | Laurell et al. | 435/287.2 |
| 2015/0093757 A1 * | 4/2015 | Gavin | 435/7.1 |
| 2015/0118249 A1 * | 4/2015 | Leach et al. | 424/158.1 |

* cited by examiner

*Primary Examiner* — Bernard E Souw
(74) *Attorney, Agent, or Firm* — Haukaas Fish PLLC; Michael H. Haukaas

(57) ABSTRACT

Described herein is a method and system for on-line coupling of capillary isoelectric focusing (cIEF) to high-resolution mass spectrometry in which a sheath flow buffer comprising polar organic solvent and organic acid is used as both an immobilization solution for (cIEF) and an ionization solution for electrospray ionization (ESI).

20 Claims, 6 Drawing Sheets

METHOD FOR ANALYZING SAMPLE COMPONENTS

CROSS-REFERENCE TO RELATED APPLICATIONS

This application is a U.S. National Stage application of International Application No. PCT/US2013/039286, filed on May 2, 2013, said International Application No. PCT/US2013/039286 claims benefit under 35 U.S.C. §119(e) of the U.S. Provisional Application No. 61/641,975, filed May 3, 2012. Each of the above listed applications is incorporated by reference herein in its entirety for all purposes.

BACKGROUND OF THE INVENTION

Recombinant proteins are becoming increasingly important as therapeutics. Recombinant proteins can be manufactured using cell lines, for example non-human mammalian host cell lines, which are engineered to express certain human gene sequences to produce a protein of interest. After the target protein is produced in the cell culture, it can be purified through known processes to high levels of purity. However, trace amounts of contaminant proteins produced by the host cell line (called Host Cell Proteins, or HCP) can be present in the depleted cell culture.

HCP can potentially impact product quality and safety. Consequently, it is important to characterize HCP present in therapeutic products to mitigate these risks. Current characterization methods for HCP, such as two-dimensional gel electrophoresis, tend to be labor-intensive and cumbersome, which can limit the use of these methods for HCP characterization, particularly during commercial production.

Electrophoresis refers to the differential movement or migration of ions by attraction or repulsion in an electric field. Capillary isoelectric focusing (cIEF) is a high-resolution separation technique based on differences in isoelectric points (pI) of sample components and is suitable for use for separation of amphoteric substances such as amino acids, peptides and pharmaceuticals. In cIEF, proteins migrate, under the influence of an electrical field, through a pH gradient created by carrier ampholytes (CA). Ampholytes that are positively charged migrate toward the cathode, while those that are negatively charged migrate towards the anode. Consequently, the pH increases toward the cathode end of the capillary and decreases toward the anode end. When an ampholyte reaches its own pI and is no longer charged, migration ceases, resulting in the formation of a stable pH gradient. An amphoteric analyte will eventually encounter a pH at which it has a zero net charge and will therefore cease to migrate, resulting in a focusing or separation of analytes by pI. cIEF has been coupled with a number of detection techniques, including UV absorbance, laser induced fluorescence and mass spectrometry (MS).

Mass spectrometry (MS) is an analytical technique in which chemical compounds are ionized to generate charged molecules or molecule fragments which are then separated according to their mass-to-charge ratio in an analyzer using an electromagnetic field. The separated ions can then be detected and analyzed.

Atmospheric Pressure Ionization (API) sources can be used to ionize sample molecules at atmospheric pressure and then transfer the ions into a mass spectrometer. API is suitable for ionization of thermally labile samples such as polymers and peptides. Electrospray Ionization (ESI) is an API application that is frequently used for MS of thermally labile and high molecular weight compounds, such as polymers and peptides, which are low- or non-volatile.

However, on-line coupling of cIEF with ESI-MS for biological samples, especially protein digests, has been challenging. Therefore, there is a need for an improved on-line coupling of cIEF with ESI-MS for biological samples.

SUMMARY OF THE INVENTION

Described herein is a method for identifying and analyzing one or more components in a sample. In one embodiment, the sample includes a heterogeneous mixture of biomolecules. In another embodiment, the sample includes recombinant protein depleted cell culture. In a more specific embodiment, one or more components include host cell protein. In one embodiment, the sample includes recombinant monoclonal antibody depleted cell culture and one or more sample components include host cell proteins. In a more particular embodiment, the invention provides a method for identifying host cell protein (HCP) components in a depleted cell culture sample.

In one embodiment, the method includes steps of: (a) separating one or more components in the sample by capillary isoelectric focusing (cIEF); (b) transferring the separated components from the separation chamber to an ionization instrument using a sheath flow solution; (c) ionizing the sample components; and (d) identifying and analyzing one or more components in the sample by mass spectrometry (MS). In one embodiment, the ionization instrument includes an electrospray ionization (ESI) instrument.

In the method of the invention, the sheath flow solution serves as both a mobilization solution for the separation chamber and an ionization solution for the ionization instrument. In a more particular embodiment, the sheath flow buffer includes between about 30% and about 50% polar organic solvent and between about 0.01% and 0.1% organic acid. The polar organic solvent can be a polar protic solvent or a polar aprotic solvent. In one embodiment, the polar protic solvent includes an aliphatic alcohol, for example, methanol, ethanol, propanol, butanol, isopropyl alcohol, and combinations thereof. In another embodiment, the polar aprotic solvent includes acetonitrile. In one embodiment, the organic acid is selected from formic acid, acetic acid, ethanoic acid, propanoic acid, benzoic acid, and combinations thereof. In one embodiment, the organic acid has a pKa between about 4.0 and 5.0. In a more particular embodiment, the sheath flow solution includes between about 30% and about 50% aliphatic alcohol and between about 0.01% and 0.1% formic acid. In one embodiment, the sheath flow solution includes between about 30% and about 50% methanol and between about 0.01% and 0.1% formic acid.

In one embodiment, separating includes steps of: (a) introducing a volume of the sample and an ampholyte buffer into the separation chamber, wherein the separation chamber includes a capillary; and (b) focusing the sample and ampholyte buffer in the separation capillary under a focusing voltage of up to about 50 kV. In a more particular embodiment, the focusing voltage is between about 5 kV and about 50 kV. In one embodiment, the sample is focused under an applied electric field between about 300 V/cm and about 600 V/cm. In a more particular embodiment, the applied electric field is between about 300 V/cm and about 400 V/cm.

In one embodiment, the sample is transferred to the ionization instrument under a mobilization voltage of up to about 50 kV. In a more particular embodiment, the mobilization voltage is between about 5 kV and about 50 kV. In one embodiment, the sample is transferred to the ionization instrument under an applied electric field between about 300

V/cm and about 600 V/cm. In a more particular embodiment, the sample is transferred to the ionization instrument under an applied electric field between about 300 V/cm and about 350 V/cm.

In another embodiment, the sample is transferred to the ionization instrument by hydrodynamic injection. In one embodiment, hydrodynamic injection includes application of a pressure between about 0.5 psi and about 50 psi using a syringe at the inlet of the separation chamber. In another embodiment, hydrodynamic injection includes application of a vacuum between about 0.5 psi and about 50 psi at the outlet of the separation chamber.

In one embodiment, the separation chamber is a capillary that has a volume and the volume of sample introduced is less than or equal to the capillary volume. In one embodiment, the volume of sample is between about 25% and about 100% of the volume of the capillary. In another embodiment, the volume of sample introduced is between about 1 µL and 25 µL. In one embodiment, the sample includes between about 0.1 µg/ml and 10 mg/ml, each, of one or more amphoteric sample components.

In one embodiment, the separation chamber is a capillary that is a fused silica ($SiO_2$) capillary. In one embodiment, the capillary includes a polymeric coating. In a more particular embodiment, the polymeric coating is selected from polyacrylamide (LPA), methylcellulose, polyvinyl alcohol (PVA), and combinations thereof.

In one embodiment, the ampholyte includes a carrier ampholyte (CA) selected from Ampholine™, Biolyte™, Pharmalyte™, Servalyt™, and combinations thereof. In one embodiment, the ampholyte includes between about 0.1% and about 10% Pharmalyte™. In one embodiment, the ampholyte includes narrow pH range carrier ampholyte. In one embodiment, the ampholyte include a broad pH range carrier ampholyte. In one embodiment, the ampholyte includes Pharmalyte™ selected from Pharmalyte (1-3), Pharmalyte (5-8), and Pharmalyte (3-10). In one embodiment, the ampholyte includes between about 2% and about 8% Pharmalyte (3-10) solution. In another embodiment, ampholytes are mixtures of low molecular weight molecules containing both acidic and basic functional groups, such as amino acids.

In one embodiment, the method also includes a step of digesting one or more components in the sample prior to introducing the sample into the separation capillary. In one embodiment, one or more components in the sample are digested with a proteolytic enzyme, including, for example, serine proteases, threonine proteases, cysteine proteases, aspartate proteases, metalloproteases, glutamic acid proteases, and combinations thereof. In one embodiment, one or more components in the sample are digested with trypsin. In one embodiment, the proteolytic enzyme is immobilized on a solid support. In a more specific embodiment, trypsin is immobilized on a solid support. In one embodiment, the solid support is selected from polymer particles, glass, membrane, gel beads, sol-gel supports, porous silicon matrix, porous monolithic materials, magnetic materials and combinations thereof. In one embodiment, one or more components in the sample are digested (for example by immobilized trypsin) at a temperature between about 25° C. and about 40° C., or at a temperature between about 30° C. and about 40° C. In one embodiment, one or more components in the sample are digested by incubating the sample with proteolytic enzyme for between about 1 hours and about 20 hours. In one embodiment, one or more components in the sample are digested by incubating the sample with proteolytic enzyme (for example, immobilized trypsin) for between about 30 seconds and about 30 minutes. In one embodiment, one or more components in the sample are digested by incubating the sample with proteolytic enzyme for between about 5 hours and about 15 hours. In one embodiment, one or more components in the sample are digested by incubating the sample with proteolytic enzyme for at least about 12 hours.

In one embodiment, the sample is diluted with water after digestion, combined with a carrier ampholyte and introduced into the separation chamber. In one embodiment, the sample is diluted with water at a ratio of water to sample between about 2:1 and 1:2.

In one embodiment, one or more components include protein and the method includes denaturing proteins in the sample prior to introduction of sample into the separation chamber. In one embodiment, denaturing proteins in the sample includes thermal denaturation. In one embodiment, denaturing proteins in the sample includes incubating the sample solution with a nonionic surfactant. In one embodiment, denaturing proteins in the sample includes combining the sample with a base to form a basic solution having a pH between about 8 and about 10 and incubating the proteins in the solution for at least about 5 minutes, or between about 5 minutes and about 60 minutes. In one embodiment, denaturing proteins in the sample includes incubating the sample with an acid to form an acidic solution having a pH between about 2 and about 3 and incubating the proteins in the solution for at least about 5 minutes or between about 5 minutes and about 60 minutes. In one embodiment, thermal denaturation includes incubating the sample at an elevated temperature between about 60° C. and about 80° C. for at least about 5 minutes, or between about 5 minutes and about 60 minutes. In one embodiment, denaturing the proteins in the sample includes incubating the sample with a denaturation solution including ammonium bicarbonate. In one embodiment, the denaturing solution further includes urea. In one embodiment, the denaturing solution further includes organic solvent, such as methanol or acetonitrile (ACN). In one embodiment, denaturing the proteins in the sample includes incubating the sample with a denaturation solution including organic solvent, such as methanol or acetonitrile, for about 30 minutes.

In one embodiment, the method further includes incubating the sample with a reduction solution and/or an alkylation solution. In one embodiment, the reduction solution is selected from dithiothreitol (DTT), Tris(2-carboxyethyl) phosphine (TCEP), tributyl phosphine (TBP), and combinations thereof. In one embodiment, the alkylation solution includes iodoacetamide (IAA), β-mercaptoethanol, or combinations thereof.

The invention also provides a system for interfacing capillary isoelectric focusing (cIEF) and mass spectroscopy (MS). The system includes: (a) a cIEF instrument having a separation chamber for separating and focusing one or more components in a liquid sample; (b) a voltage power supply for applying an electrical potential across the separation chamber, wherein the separation chamber contains sample and carrier ampholyte and the electrical potential separates and focuses one or more components in the sample; (c) a sheath flow solution for transferring one or more separated and focused components directly from the separation chamber of the cIEF instrument to an emitter configured to supply the solution to an electrospray ionization (ESI) instrument; and (d) a MS instrument for analyzing sample analyte.

In one embodiment, the sheath flow solution includes between about 30% and about 50% polar organic solvent and between about 0.01% and 0.1% organic acid. In one embodiment, the polar organic solvent is selected from polar protic solvents and polar aprotic solvents. In one embodiment, the polar protic solvent includes an aliphatic alcohol. In one embodiment, the aliphatic alcohol is selected from methanol, ethanol, propanol, butanol, isopropyl alcohol, and combinations thereof. In one embodiment, the polar aprotic solvent includes acetonitrile. In one embodiment, the organic acid is selected from formic acid, acetic acid, ethanoic acid, propanoic acid, benzoic acid, and combinations thereof. In one embodiment, the organic acid has a pKa between about 4.0 and 5.0. In a more particular embodiment, the sheath flow solution includes between about 30% and about 50% methanol and between about 0.01% and 0.1% formic acid.

In one embodiment, the cIEF instrument includes an anode, a cathode, an anolyte reservoir and a catholyte reservoir. In one embodiment, the anolyte reservoir contains anolyte including an acid such as phosphoric acid, formic acid, aspartic acid, or combinations thereof. In one embodiment, the catholyte reservoir contains catholyte including a base such as sodium hydroxide, potassium hydroxide, sodium carbonate, potassium carbonate or combinations thereof.

In one embodiment, the system includes an interface coupling device configured to couple an end of the separation chamber to the emitter. In one embodiment, the sheath flow solution is introduced into the anolyte and/or catholyte reservoir to mobilize the focused sample components. In one embodiment, the separation chamber includes a capillary having an anode end, wherein the anode end of the capillary is inserted into an input end of the emitter after focusing of one or more components in the sample and the sheath flow solution is introduced into the catholyte reservoir to mobilize the focused components. In another embodiment, the separation chamber includes a capillary having a cathode end, wherein the cathode end of the capillary is inserted into an input end of the emitter after focusing of one or more components in the sample and the sheath flow solution is introduced into the anolyte reservoir to mobilize the focused components.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

While the invention is susceptible to various modifications and alternative forms, specifics thereof have been shown by way of example and drawings, and will be described in detail. It should be understood, however, that the invention is not limited to the particular embodiments described. On the contrary, the intention is to second modifications, equivalents, and alternatives falling within the spirit and scope of the invention.

DETAILED DESCRIPTION

Figure 1:
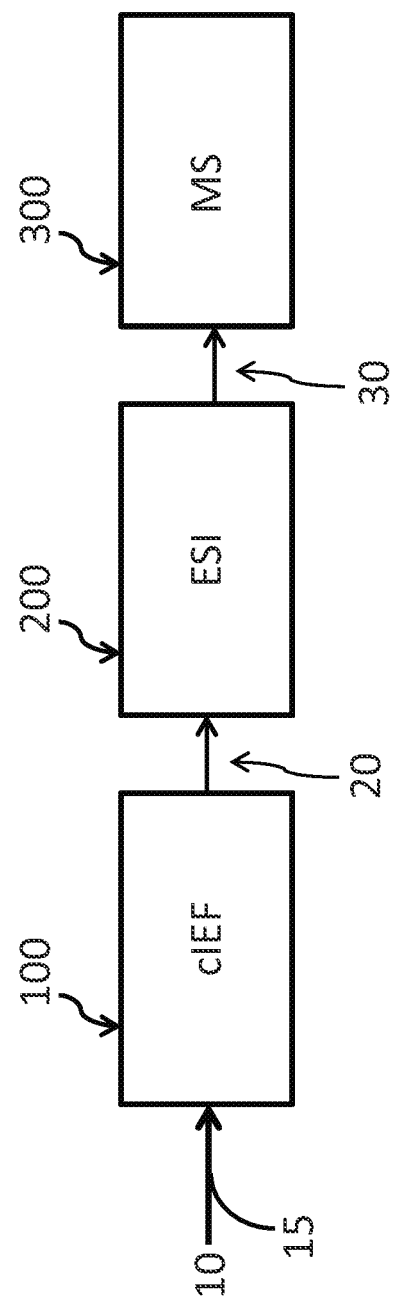
FIG. 1 is a flow chart of a combined cIEF-ESI-MS system.

Described herein is a novel system for identifying and analyzing one or more components in a sample. In one embodiment, the system is configured to detect proteins in a sample, for example, residual host cell proteins retained in a depleted cell culture sample. In particular, the system identifies and analyzes components in a sample using an online analysis and identification process that combines capillary isoelectric focusing (cIEF), electrospray ionization (ESI) and mass spectrometry (MS). A flow chart providing an overview of the combined cIEF-ESI-MS system is shown in FIG. 1. Briefly, a "focusing solution" 10 is prepared that includes a mixture of a sample solution 15 that may contain one or more analytes (also referred to as sample components herein) of interest, for example HCP, and one or more other components. The focusing solution 10 is introduced into the cIEF instrument 100 for separation. After the sample components are separated by cIEF 100, an ionization solution 20, which contains the separated components is introduced into the ESI instrument 200 for ionization. The ionized components 30 can then be analyzed by MS 300.

The online process described herein is able to substantially reduce the total analysis time for the combined cIEF-ESI-MS process; whereas a typical process can take upwards of 10 hours (including sample preparation, digestion, separation and detection), the combined process described herein is able to reduce the time to complete the entire process to less than about 5 hours, less than about 4 hours, less than about 3 hours, or less than about 2 hours. A further advantage is that cIEF can enrich the sample more than 10 fold. According to the invention described herein, a sheath flow liquid serves as both a chemical mobilization solution for cIEF and an ionization solution for ESI.

Overview of Capillary Isoelectric Focusing (cIEF)

As used herein, the term "electrophoresis" refers to the migration of ions under the influence (attraction or repulsion) of an electric field. The simplest electrophoretic separations are based on ion charge/size.

Capillary Isoelectric focusing (cIEF) is an electrophoretic technique in which amphoteric components in a sample are separated based on differences in isoelectric points (pI). Under the influence of an electrical field, a pH gradient is formed by a series of zwitterions (also called ampholytes) within a separation chamber, for example, a capillary. Amphoteric sample components (which can also be called analytes) in a sample migrate in the electric field until they reach a point in the pH gradient where their pH equals their pI (i.e., where the molecule has no net charge because positive and negative charges cancel out to zero). At this point, the amphoteric components cease to move and are focused. After focusing, a mobilization step passes the focused analytes out of the separation chamber for analysis. In general, analytes with pIs that differ by less than 0.05 pH unit can be resolved by cIEF.

Many types of compounds can be separated by cIEF, including but not limited to, peptides, amino acids, nucleic acids (DNA and RNA), inorganic ions, organic bases, organic acids, and whole cells. As used herein, the term "peptide" refers to a compound that includes two or more amino acids linked in a chain wherein the carboxyl group of each amino acid is joined to the amino group of the neighboring amino acid. Examples of peptides include, but are not limited to oligopeptides (i.e., a continuous unbranched peptide, usually containing between 2 and 10 amino acid residues), polypeptides (i.e., a continuous unbranched peptide, usually containing more than 10 amino acid residues) and macromolecular proteins, which may include one or more polypeptide chains folded into a specific spatial conformation. The term "primary structure" refers to the amino acid sequence of a polypeptide chain in a protein. The term "secondary structure" refers to highly regular sub-structures, including, for example, alpha helixes and beta sheets. "Tertiary structure" refers to a three-dimensional structure of a single protein molecule and "quaternary structure" refers to an assembly of several protein subunits.

The amino acid residues present on peptides can impart amphoteric properties the molecule, such that the molecules contain both positive and negative charges. The net charge of a peptide depends upon the pendant functional groups and the pH of the surrounding environment. In general, peptides are positively charged at pH values below their pIs and negatively charged at pH values above their pIs. Consequently, during electrophoresis individual peptides will migrate toward a region where the pH is equal to their pIs. cIEF is therefore useful for analysis and/or characterization of complex protein mixtures, for example, HCP in depleted cell culture media. cIEF can also be used to monitor product processing, study formulations and perform quality control for recombinantly produced proteins. cIEF can also be used for prefractionation of complex protein mixture.

cIEF Instrumentation

Figure 2:
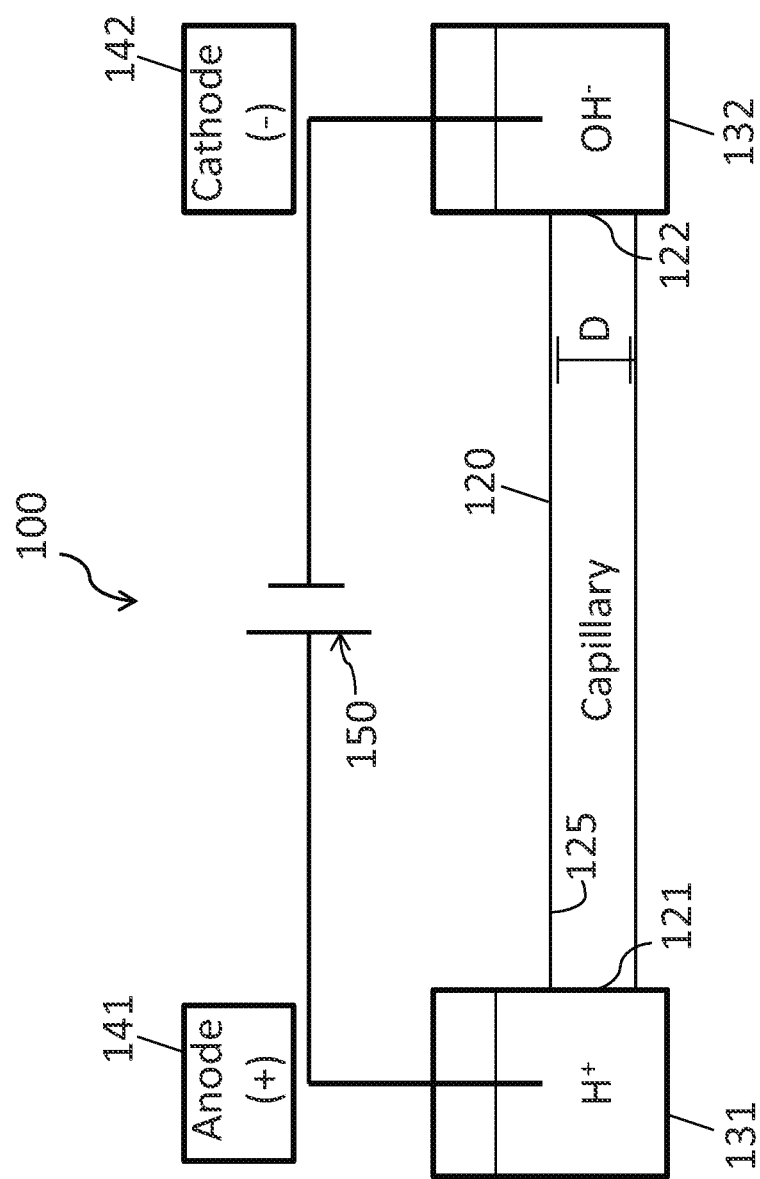
FIG. 2 is a schematic representation of cIEF.

The basic instrument set up for cIEF is shown schematically in FIG. 2 and includes a separation chamber 120, two buffer reservoirs 131, 132, and two electrodes 141, 142 and a power supply 150. The separation chamber 120 is typically an elongate capillary with an inner wall 125 that defines a lumen having a diameter (D) that extends between an inlet 121 and an outlet 122. In one embodiment, the inlet 121 of the separation chamber 120 is in fluid communication with a first buffer reservoir 131 and the outlet 122 of the separation chamber is in fluid communication with a second buffer reservoir 132.

In one embodiment, the separation chamber 120 is a glass capillary with a length of at least about 5 cm, at least about 10 cm, at least about 15 cm, at least about 20 cm, at least about 25 cm, at least about 30 cm, at least about 35 cm, at least about 40 cm, at least about 45 cm, at least about 50 cm, and up to about 55 cm, up to about 60 cm, up to about 65 cm, up to about 70 cm, up to about 75 cm, up to about 80 cm, up to about 85 cm, up to about 90 cm, up to about 95 cm, or up to about 100 cm and an internal diameter of at least about 10 µm, at least about 15 µm, at least about 20 µm, at least about 25 µm, at least about 30 µm, at least about 35 µm, at least about 40 µm, at least about 45 µm, or at least about 50 µm, and up to about 50 µm, up to about 75 µm, up to about 100 µm, up to about 125 µm and up to about 150 µm. In one embodiment, the separation chamber 120 is a fused silica capillary. In another embodiment, the separation chamber 120 is constructed from Teflon™ or borosilicate glass. In another embodiment, the separation chamber may be a channel in a planar structure formed using well-known microfabrication technologies. In this case, the device may be made from glass, fused silica, or polymers such as polydimethylsilane (PDMS). In some instances, fused silica may be preferred since it is transparent over a wide range of the electromagnetic spectrum and has a high thermal conductance. Fused silica is also easy to manufacture into capillaries with diameters of a few micrometers.

In some embodiments, a bare silica material is used for the inner wall 125 of the separation chamber 120. In other embodiments, the silane groups on the inner wall 125 of the separation chamber 120 can be covalently attached with neutral or hydrophilic substituents to reduce electroosmotic flow (EOF) and/or prevent adsorption of the analyte to the inner wall 125. Examples of neutral coatings include, but are not limited to, linear polyacrylamide (LPA), polyvinyl alcohol (PVA), trimethylchlorosilane and divinylbenzene coatings. Examples of hydrophilic coatings include acrylamide (AA), dimethylacrylamide (DMA), N-acryloylaminoethoxyethanol (AAEE), or N-acryloylaminopropanol (AAP). In another embodiment, a dynamic coating can be used to reduce electroosmotic flow. The term "dynamic coating" refers to the inclusion of an additive in the separation solution that adheres tightly to the inner wall of the separation chamber and effectively reverses the direction of electroosmotic flow (EOF). Examples of dynamic coating additives include surfactants and polymers. Surfactants can include cationic surfactants such as cetyltrimethylammonium bromide (CTAB); zwitterionic surfactants, such as CHAPS, Caprylyl sulfobetaine, lauryl sulfobetaine, or palmityl sulfopetaine; and non-ionic surfactants, such as tween 20, NP 40, or Triton X. Other dynamic coating additives include polymeric additives such as hydrophilic polymers, for example, methylcellulose (MC), (hydroxypropyl)methylcellulose (HPMC), polyethylene oxide (PEO), polyethylene glycol (PEG), dextran, poly(vinyl alcohol), or poly(dimethylacrylamide). Dynamic coating additives may be included in the focusing solution at a concentration of between about 0.1% w/v and about 1.0% w/v, or at least about 0.1% w/v, at least about 0.2% w/v, at least about 0.3% w/v, at least about 0.4% w/v, and at least about 0.5% w/v and up to about 0.6% w/v, up to about 0.7% w/v, up to about 0.8% w/v, up to about 0.9% w/v, or up to about 1.0% w/v.

During cIEF, a pH gradient is formed due to the presence of the separation solution inside of the separation chamber 120, wherein the separation solution includes carrier ampholyte (CA). The term "carrier ampholyte" (CA) refers a solution that contains a variety of amphoteric components. As used herein, the term "amphoteric component" refers to a substance that can act as both an acid or a base. The resolving power of an ampholyte pH gradient is influenced by the number of ampholyte species in the solution. In general, the greater the number of ampholytes, the smaller the pH variance between adjacent loci within the separation chamber 120, such that the pH gradient is smoother when a larger number of ampholytes are used. Some commercially available CAs can contain over 900 amphoteric components.

CAs can be broad (i.e., encompass multiple pH units) or narrow (i.e., encompass only a few pH units). As used herein, the term "broad" refers to a CA that encompasses at least about 4 pH units, at least about 5 pH units, at least about 6 pH units and up to about 7 pH units, or up to about 8 pH units. As used herein, the term "narrow" refers to a CA that encompasses less than about 4 pH units, less than about 3 pH units, less than about 2 pH units, less than about 1 pH unit, or less than about 0.5 pH units. In general, the ampholyte composition is selected based upon the desired pI separation range. Typically, a broad CA is chosen for a sample of unknown pI value. However, in situations where an enhanced resolution of proteins with similar pI values is desired, the use of narrow range CA mixtures may be desirable.

In general, there are four commercially available CAs: Pharmalyte™ (GE Healthcare, Pittsburgh, Pa.), Bio-lyte™ (Bio Rad, Hercules, Calif.), Servalyt™ (Biophoretics, Inc., Reno, Nev.) and Ampholine™ (GE Healthcare, Pittsburgh, Pa.).

Pharmalyte™ is an ampholyte buffer available in a broad pH range (between about 3 and about 10) and various narrow pH ranges (between about 2.5 and about 5; between about 4 and about 6.5; between about 5 and about 8; between about 8 and about 10.5; between about 4.2 and about 4.9; between about 4.5 and about 5.4; between about 5 and about 6; and between about 6.7 and about 7.7) for use in cIEF. In some instances, particularly when using cIEF, it may be desirable to use a CA that has low background UV absorption. Pharmalyte™ may therefore be desirable, due to its low background UV absorption along its entire pH gradient.

Bio-Lyte™ is an ampholyte buffer available in a broad pH range (between about 3.5 and about 9.5) and various narrow ranges (between about 3 and about 5; between about 4 and about 6; between about 5 and about 7; between about 5 and about 8; between about 6 and about 8; between about 7 and about 9; and between about 8 and about 10) for use in cIEF.

Servalyt™ carrier ampholytes are low molecular weight molecules of zwitterionic character. They are a mixture of synthetically derived species of average molecular weight distribution of 400 to 1000 dalton and come in a variety of pH ranges including narrow pH ranges (between about 2 and about 4; between about 3 and about 4; between about 3 and about 5; between about 3 and about 6; between about 4 and about 5; between about 4 and about 6; between about 4 and about 7; between about 5 and about 6; between about 5 and about 7; between about 5 and about 8; between about 6 and about 7; between about 6 and about 8; between about 6 and about 9; between about 7 and about 9; and between about 9 and about 11) and broad pH ranges (between about 2 and about 9; between about 2 and about 11; between about 3 and about 7; between about 3 and about 10; between about 4 and about 9; between about 5 and about 9).

Ampholine™ is an ampholyte buffer that includes various polyamino-polycarboxylic acids of low molecular weight and covers a pH range 3.5 to 10. However, Ampholine™ production was discontinued in 2007.

In one embodiment, the separation solution includes between about 0.1% and about 10% CA, between about 0.1% and 1.0% CA or between about 0.2% and 0.8% CA. In other embodiments, the separation solution includes between about 1% and 10% CA or between about 2% and about 8% CA. As used herein 100% refers to a stock solution of CA. In a more specific embodiment, the separation solution includes at least about 0.1%, at least about 0.2%, at least about 0.3%, at least about 0.4% and up to about 0.5%, up to about 0.6%, up to about 0.7% and up to about 0.8%, up to about 0.9%, or up to about 1% CA. In another embodiment, the separation solution includes at least about 1%, at least about 2%, at least about 3%, at least about 4% and up to about 5%, up to about 6%, up to about 7%, up to about 8%, up to about 9%, and up to about 10% CA. In one embodiment, the CA is diluted with an inert diluent, such as deionized water, ammonium bicarbonate, ammonium acetic, or other buffer.

The buffer in the reservoir 131 proximate the anode 141 is has a low pH (i.e., is an acid) and is referred to herein as the "anolyte buffer." Generally, the pH of the anolyte buffer is less than about 7, less than about 6.5, less than about 6, less than about 5.5, less than about 5, less than about 4.5, less than about 4, less than about 3.5, less than about 3, less than about 2.5 or less than about 2. The buffer in the reservoir 132 proximate the cathode 142 has a high pH (i.e., is a base) and is referred to herein as the "catholyte buffer." Generally, the pH of the catholyte buffer is more than about 7, more than about 7.5, more than about 8, more than about 8.5, more than about 9, more than about 9.5, more than about 10, more than about 10.5, more than about 11, more than about 11.5, or more than about 12.

Examples of suitable anolyte buffers include formic acid, phosphoric acid, aspartic acid, or combinations thereof. In one embodiment, the anolyte buffer includes between about 50 mM and 500 mM acid, generally at least about 50 mM, at least about 100 mM, at least about 150 mM, at least about 200 mM, or at least about 250 mM, and up to about 250 mM, up to about 300 mM, up to about 350 mM, up to about 400 mM, up to about 450 mM, or up to about 500 mM acid. In a more particular embodiment, the anolyte buffer includes between about 50 mM and 500 mM phosphoric acid, generally at least about 50 mM, at least about 100 mM, at least about 150 mM, at least about 200 mM, or at least about 250 mM, and up to about 250 mM, up to about 300 mM, up to about 350 mM, up to about 400 mM, up to about 450 mM, or up to about 500 mM phosphoric acid. In one embodiment, the anolyte buffer can include an anodic stabilizer, such as iminodiacetic acid. In one embodiment, the anolyte buffer includes between about 50 mM and 500 mM stabilizer, such as iminodiacetic acid, generally at least about 50 mM, at least about 100 mM, at least about 150 mM, at least about 200 mM, or at least about 250 mM, and up to about 250 mM, up to about 300 mM, up to about 350 mM, up to about 400 mM, up to about 450 mM, or up to about 500 mM stabilizer, such as iminodiacetic acid.

Examples of suitable catholyte buffers include, but are not limited to, sodium hydroxide, potassium hydroxide, ammonium hydroxide, sodium carbonate, lysine, potassium carbonate, and combinations thereof. In one embodiment, the catholyte buffer includes between about 50 mM and 500 mM base, generally at least about 50 mM, at least about 100 mM, at least about 150 mM, at least about 200 mM, or at least about 250 mM, and up to about 250 mM, up to about 300 mM, up to about 350 mM, up to about 400 mM, up to about 450 mM, or up to about 500 mM base. In one embodiment, the catholyte buffer includes between about 50 mM and 500 mM sodium hydroxide, generally at least about 50 mM, at least about 100 mM, at least about 150 mM, at least about 200 mM, or at least about 250 mM, and up to about 250 mM, up to about 300 mM, up to about 350 mM, up to about 400 mM, up to about 450 mM, or up to about 500 mM sodium hydroxide. In a more specific embodiment, the anolyte buffer includes between about 0.01% v/v and about 5% v/v acid, or at least about 0.01% v/v, at least about 0.05% v/v, at least about 0.1% v/v, at least about 0.5% v/v, and up to about 0.5% v/v, up to about 1% v/v, up to about 5% v/v acid. In one embodiment, the catholyte buffer includes between about 0.01% v/v and about 5% v/v base, or at least about 0.01% v/v, at least about 0.05% v/v, at least about 0.1% v/v, at least about 0.5% v/v, and up to about 0.5% v/v, up to about 1% v/v, up to about 5% v/v base. In some embodiments, the catholyte buffer includes a cathodic stabilizer, for example, arginine. In one embodiment, the catholyte buffer includes between about 100 mM and 500 mM of a stabilizer such as arginine, generally at least about 50 mM, at least about 100 mM, at least about 150 mM, at least about 200 mM, or at least about 250 mM, and up to about 250 mM, up to about 300 mM, up to about 350 mM, up to about 400 mM, up to about 450 mM, or up to about 500 mM stabilizer, such as arginine. During operation of cIEF, a pH gradient is formed within the separation chamber between the anode and cathode 141, 142.

Any suitable power supply can be used for cIEF. Generally, a high-voltage dc power supply with a voltage between about 1 kV to about 50 kV is used, for example, a power supply with a voltage of at least about 1 kV, at least about 5 kV, at least about 10 kV, at least about 15 kV, at least about 20 kV, and at least about 25 kV and/or up to about 20 kV, up to about 25 kV, up to about 30 kV, up to about 35 kV, up to about 40 kV, up to about 45 kV or up to about 50 kV. The generated electric field is generally at least about 300 V/cm, at least about 325 V/cm, at least about 350 V/cm, at least about 375 V/cm and up to about 400 V/cm, up to about 425 V/cm, up to about 450 V/cm, up to about 475 V/cm, up to about 500 V/cm, up to about 525 V/cm, up to about 550 V/cm, up to about 575 V/cm, or up to about 600 V/cm.

In one embodiment, the cIEF instrument is a Beckman-Coulter P/ACE MDQ Capillary Electrophoresis System (Beckman-Coulter Instruments, Inc., Fullterton, Calif.).

In general, cIEF can be broken down into five stages:
1. sample preparation;
2. introduction of sample into the separation chamber;
3. focusing of the sample in the separation chamber under an applied voltage;
4. mobilization of the focused sample out of the separation chamber; and
5. detection and analysis of the focused and mobilized sample.

When developing a cIEF process, several parameters can be varied to improve process performance, including, for example, the composition of the anolyte and catholyte buffers, separation chamber dimensions and material, carrier ampholyte, focusing time and voltage, mobilization method, sample concentration, and the inclusion or exclusion of other additives.

Sample Preparation

The system and method described herein can be used to detect components in a sample, for example, proteins in a sample, such as Host Cell Proteins (HCP) in depleted cell culture medium. As used herein, the term "depleted" cell culture media refers to the flow through fraction of cell culture media from a purification process after the recombinant protein of interest has been removed. In one embodiment, the sample is the depleted cell culture media from a recombinant monoclonal antibody cell culture.

Protein purification varies from simple one-step precipitation procedures to large scale production processes. Often more than one purification step is used to obtain a product with the desired level of purity. Many purification schemes involve some form of chromatography. Different chromatography techniques with different selectivities can form powerful combinations for the purification of biomolecules. Many purification protocols require more than one step to achieve the desired level of product purity. Generally, purification protocols have three phases: (1) the capture phase, in which the target product is isolated and concentrated; (2) intermediate purification, in which most of the bulk impurities are removed; and (3) polishing, in which trace impurities are removed. Once the recombinant protein is purified from the cell culture, the depleted (flow through) fraction can then be analyzed for HCP.

Protein Denaturation

In their native form, proteins fold into a variety of shapes, some compact, some elongated. The rate of migration of native proteins through a sieving medium is therefore more a reflection of their relative compactness, and not so much an accurate measure of molecular weight. As used herein, "protein denaturation" refers to any noncovalent change in the structure of a protein that alters the secondary, tertiary or quaternary structure of the protein molecule. Denaturing the proteins nullifies structural affects on mobility, allowing separation on a true charge/mass ratio basis. Denaturation also separates subunits in multimeric proteins, allowing analysis of large, complex aggregates. Additionally, most native proteins are resistant to the action of proteolytic enzymes. Protein denaturation alters the structure of the protein and can expose the proper groups to the proteolytic enzymes, and hence increase proteolysis. Thus, protein molecules are often denatured prior to electrophoresis.

Many methods for denaturing proteins are known and can be used in connection with the system and method of the invention. One example of a common denaturant is a detergent, such as an anionic surfactant, for example, sodium dodecyl sulfate (SDS) or sodium deoxycholate (SDC), or a nonionic surfactant, such as NP40, TWEEN 20, or Triton X. Generally, proteins can be denatured by incubating a protein solution with a surfactants at a concentration of surfactant between about 0.1 mM and about 50 mM, generally at least about 0.1 mM, at least about 0.2 mM, at least about 0.3 mM, at least about 0.4 mM, at least about 0.5 mM, at least about 0.6 mM, at least about 0.7 mM, at least about 0.8 mM, at least about 0.9 mM, or at least about 1.0 mM, and up to about 1 mM, up to about 5 mM, up to about 10 mM, up to about 15 mM, up to about 20 mM, up to about 25 mM, or up to about 50 mM. Thermal denaturation is another known method for denaturing proteins. Generally, proteins can be denatured by incubating them at a temperature of at least about 50° C., at least about 55° C., at least about 60° C., at least about 65° C., at least about 70° C., and up to about 75° C., up to about 80° C., up to about 85° C., and up to about 90° C. for at least about 1 minute, at least about 5 minutes, at least about 10 minutes, at least about 15 minutes, and up to about 30 minutes, up to about 45 minutes, or up to about 60 minutes. Depending upon the protein studied and the severity of the heating, thermal denaturation may or may not be reversible. Proteins in the sample can also be denatured by combining the sample solution with an acid to form an acid solution having a pH between about 2 or about 3. Examples of suitable acids include, but are not limited to, guanidine hydrochloride. In another embodiment, proteins in the sample can be denatured by combining the sample solution with a base to form a base solution having a pH between about 8 and about 10. Examples of suitable bases include, but are not limited to, urea. In still another embodiment, the proteins in the sample solution can be denatured by combining the sample solution with a solution having a high salt concentration, such as NaCl or LiCl at concentrations from 2 M to 5 M. In one embodiment the salt is removed from the protein before isoelectric focusing (for example, by size exclusion chromatography).

Since disulfide bonds can also hinder proteolysis, known reduction and alkylation processes can also be used to assist in the complete denaturation of protein in a sample. The term "reduction" refers to the reduction of disulfide bonds, and can be accomplished by incubating the denatured protein with a reducing agent such as dithiothreitol (DTT), 2-mercaptoethanol (BME), tris(2-carboxyethyl)phosphine chloride (TCEP), or tributylphosphine (TBP) [others?]. Generally, proteins are reduced by incubating a protein sample in a solution containing between about 0.1 mM and 10 mM reducing agent, generally at least about 0.1 mM, at least about 0.2 mM, at least about 0.3 mM, at least about 0.4 mM, or at least about 0.5 mM reducing agent, and up to about 1 mM, up to about 5 mM or up to about 10 mM reducing agent. Alkylation refers to alkylation of thiols and can be accomplished by incubating the denatured protein with an alkylating agent, such as ethylmaleimide (NEM), iodoacetamide (IAM), 4-vinylpyridine, or iodoacetic acid (IAA) methyl methanethiosulfonate (MMTS). Generally, a protein sample is incubated in a solution containing between about between about 10 mM and 500 mM alkylating agent, generally at least about 10 mM, at least about 20 mM, at least about 30 mM, at least about 40 mM, or at least about 50 mM alkylating agent, and up to about 100 mM, up to about 200 mM, up to about 300 mM, up to about 400, or up to about 500 mM alkylating agent.

Digestion

In some instances, it may be desirable to digest the proteins in the sample prior to electrophoresis. Many methods for protein digestion are known and include, for example, proteolysis. The term "proteolysis" refers to the digestion of proteins by enzymes called proteases (or proteolytic enzymes), including, for example, serine proteases, threonine proteases, cysteine proteases, aspartate proteases, metalloproteases, glutamic acid proteases and combinations thereof. Examples of serine proteases include trypsin, and chymotrypsin. Examples of cysteine proteases include papain. Other proteases include Lys-C, Glu-C, and Asp-N. In a more specific embodiment, protein in the sample is digested by trypsin. In one embodiment, the proteolytic enzyme is immobilized on a solid support. In a further embodiment, trypsin is immobilized on a solid support. Advantageously, immobilized trypsin can be used for trace amount (low nM or ng) protein digestion. Examples of solid supports include, but are not limited to, polymer particles, glass, membrane, gel beads, sol-gel supports, porous silicon matrix, porous monolithic materials and magnetic materials. Generally, proteins are digested by incubating a protein containing sample solution with a protease at a protease to protein ratio of at least about 1:5, at least about 1:10, at least about 1:15, at least about 1:20, at least about 1:25, at least about 1:30, and up to about 1:40, up to about 1:50, up to about 1:75, or up to about 1:100. Ratios may be higher for immobilized trypsin, for example greater than 1:100. In one embodiment, the sample solution is incubated with a proteolytic enzyme for between about 5 hours and 20 hours, or at least about 5 hours, at least about 10 hours, at least about 11 hours, at least about 12 hours, at least about 13 hours, at least about 14 hours, at least about 15 hours, and up to about 15 hours or up to about 20 hours. Generally, the digestion is performed at a temperature of at least about 25° C., at least about 30° C., at least about 35° C., and up to about 40° C., up to about 45° C. or up to about 50° C.

Preparation of a Focusing Solution

The term "focusing solution" as used herein refers to the solution containing the sample that is introduced into the cIEF separation chamber. The focusing solution can include a mixture of the sample solution and one or more other components, including, for example, carrier ampholyte (CA), an inert diluent such as distilled or deionized water, or other additives. In one embodiment, the sample solution includes depleted cell culture media.

Carrier Ampholyte (CA)

In one embodiment, the focusing solution includes carrier ampholyte (CA). As discussed above, there are four commercially available CAs: Pharmalyte™ (GE Healthcare, Pittsburgh, Pa.), Bio-lyte™ (Bio Rad, Hercules, Calif.), Servalyt™ (Biophoretics, Inc., Reno, Nev.) and Ampholine™ (GE Healthcare, Pittsburgh, Pa.). In general, the focusing solution includes between about 0.1% and about 10% CA. In one embodiment, the focusing solution includes at least about 0.1%, at least about 0.2%, at least about 0.3%, at least about 0.4%, at least about 0.5%, and up to about 0.6%, up to about 0.7%, up to about 0.8%, up to about 0.9% or up to about 1.0% CA. In other embodiments, the focusing solution includes at least about 1%, at least about 2%, at least about 3%, at least about 4%, at least about 5%, and up to about 6%, up to about 7%, up to about 8%, up to about 9% or up to about 10% CA. In other embodiments, the focusing solution does not include carrier ampholyte.

Salt Concentration

Another parameter that may be adjusted prior to introduction of the focusing solution into the separation chamber is ionic strength. The term "ionic strength" refers to the concentration of ions in a solution. For cIEF it may be desirable to have a low ionic strength, for example, less than about 100 mM, less than about 75 mM, less than about 50 mM, less than about 40 mM, less than about 30 mM, less than about 20 mM. In general, as salt concentration increases, the risk of protein precipitation occurring during focusing increases. The ionic strength of the sample solution can be modified, for example, by known desalting processes, including, for example, dilution, dialysis, gel filtration, ultra-filtration, and solid phase extraction (SPE) (e.g. Ziptip™).

Dilution of Sample

In general, a final concentration of at least about 0.1 µg/mL per protein, at least about 0.5 µg/mL per protein, at least about 1 µg/mL per protein, at least about 5 µg/mL per protein, at least about 10 µg/mL per protein, at least about 50 µg/mL per protein, at least about 0.1 mg/mL per protein, at least about 0.5 mg/mL per protein, at least about 1 mg/ml per protein, at least about 5 mg/ml per protein, and up to about 10 mg/ml per protein is desirable to attain sufficient sensitivity, focusing and mobilization using cIEF.

To obtain a desirable protein concentration, the sample solution 15 may be combined with a diluent to form a focusing solution 10 which is then introduced into the separation chamber 120. In one embodiment, the diluent is a carrier ampholyte solution and a focusing solution is prepared by mixing a sample solution containing one or more sample components and a carrier ampholyte solution, for example, at a ratio of sample solution to carrier ampholyte solution of between about 5:1 and about 1:5, between about 2:1 and about 1:2; or between about 1.5:1 and about 1:1.5, or at about 1:1. In another embodiment the ratio of sample solution to carrier ampholyte can be between about 100:1 and about 1:1, or between about 60:1 and about 1:1, or between about 100:1 and about 10:1. In another embodiment, a focusing solution is prepared by combining a sample solution containing one or more analyte components with an inert diluent, such as deionized water at a ratio of sample solution to diluent of from about 5:1 to about 1:5, from about 2:1 to about 1:2; from about 1.5:15 to about 1:1.5, or about 1:1.

In one embodiment, the protein solution is concentrated before cIEF, for example by a lyophilizing procedure.

Other Additives

At the completion of cIEF, the components of the sample are focused into narrow zones within the separation chamber and are concentrated hundreds of times. Confining proteins at their pI points (zero net charge) and at high concentrations may increase the likelihood of precipitation and/or aggregation. Therefore, it may be desirable to include one or more additives in the focusing solution to reduce precipitation and/or aggregation, including, for example, urea, sugars, and nonionic or zwitterionic surfactants.

In one embodiment, urea is included in the focusing solution to improve protein solubility. In a more specific embodiment urea is included in the focusing solution at a concentration of between about 0.1M and about 20M, or at least about 0.1M, at least about 0.5M, at least about 1M and up to about 5M, up to about 10 M, up to about 15M, or up to about 20M.

Sample Loading

Typically, before the focusing solution 10 is introduced into the separation chamber 120, the chamber 120 is prepared with one or more preconditioning rinses. In one embodiment in which the chamber 120 includes a covalent polymeric coating, the separation chamber 120 is rinsed with 5 to 10 volumes of a solvent, such as an organic solvent, for example a polar organic solvent prior to introduction of the focusing solution. The term "polar organic solvent" includes both polar protic solvents and polar aprotic solvents. As used herein, the term "polar protic solvent" refers to a solvent that has a dissociable hydrogen, for example, an alcohol that includes a hydrogen atom bound to an oxygen atom. The term "polar aprotic solvent" refers to a solvent that lacks an acidic hydrogen. Examples of suitable alcohols include aliphatic alcohols such as methanol, ethanol, propanol, butanol, isopropyl alcohol, and combinations thereof. In another embodiment, in which the separation chamber 120 is uncoated, the separation chamber 120 can be rinsed with 10 to 15 volumes of anolyte buffer, for example, phosphoric acid, formic acid, aspartic acid, or combinations thereof; or catholyte buffer, for example, sodium hydroxide, potassium hydroxide, sodium carbonate, potassium carbonate, or combinations thereof. If desired, the separation chamber 120 can also be rinsed with 10 to 15 volumes of deionized water and/or 5 to 10 volumes of the separation solution. Generally, the preconditioning fluids are conveyed through the separation chamber either by applying pressure at the inlet 121 of the separation chamber 120, for example, by use of a syringe pump at a pressure between about 0.5 psi and about 50 psi, or by reducing pressure at the outlet 122 of the separation chamber 122, for example, by application of a vacuum at a pressure between about 0.5 psi and about 50 psi. The flow rate for the preconditioning rinse is generally at least about 1 μL/min, or at least about 2 μL/min, and up to about 3 μL/min, up to about 4 μL/min, or up to about 5 μL/min.

Once the separation chamber 120 is ready, the focusing solution 10 can be introduced. Two commonly used injection methods include hydrodynamic injection and electrokinetic injection. Hydrodynamic injection is accomplished by the application of a pressure difference between about 0.5 psi and about 50 psi between the two ends of the separation chamber 120, i.e., by the use of a syringe at the inlet 121 or a vacuum at the outlet 122. Electrokinetic injection is performed by temporarily replacing one of the anolyte or catholyte buffer reservoirs 131, 132 with a reservoir that contains the focusing solution 10 and turning on the voltage for a certain period of time. In one embodiment, the focusing solution 10 is introduced by applying a voltage between about 1 kV to about 50 kV is typically used, for example, at least about 1 kV, at least about 5 kV, at least about 10 kV, at least about 15 kV, at least about 20 kV, and at least about 25 kV and/or up to about 20 kV, up to about 25 kV, up to about 30 kV, up to about 35 kV, up to about 40 kV, up to about 45 kV, or up to about 50 kV. The focusing voltage is generally at least about 300 V/cm, at least about 325 V/cm, at least about 350 V/cm, at least about 375 V/cm and up to about 400 V/cm, up to about 425 V/cm, up to about 450 V/cm, up to about 475 V/cm, up to about 500 V/cm, up to about 550 V/cm, or up to about 600 V/cm. During electrokinetic injection, the voltage is generally applied for between about 1 minute and about 30 minutes, for example, at least about 1 minute, at least about 5 minutes, at least about 10 minutes, at least about 15 minutes, and up to about 10 minutes, up to about 15 minutes, up to about 20 minutes, up to about 25 minutes, or up to about 30 minutes. The specific amount of sample introduced can be controlled by controlling injection pressure, injection voltage and/or injection time.

In one embodiment, the focusing solution 10 is combined with a separation solution prior to introduction into the separation chamber 120. In an alternate embodiment, the separation chamber 120 is first filled with separation solution and then the focusing solution 10 is introduced into the separation chamber 120. In still another embodiment, the separation chamber 120 is partially filled with the separation solution, then the focusing solution 10 is injected and then the remainder of the separation chamber 120 is filled with the separation solution.

A sufficient amount of focusing solution 10 should be loaded into the focusing chamber 120 such that the focusing chamber 120 contains a homogeneous mixture of sample. In one embodiment, the separation chamber 120 is injected with a volume of focusing solution 10 that is less than or equivalent to the volume defined by the inner surface 125 of the separation chamber 120. In one embodiment, the separation chamber 120 is injected with a volume of focusing solution 10 that is between about 25% and about 100% of the volume of the separation chamber, in particular, at least about 25%, at least about 30%, at least about 35%, at least about 40%, at least about 45%, or at least about 50%, and up to about 50%, up to about 75%, up to about 80%, up to about 85%, up to about 90%, up to about 95%, or up to about 100% of the volume of the separation chamber. In general, the volume of focusing solution injected into the separation chamber 120 will vary with the dimension of the chamber. However, in general, the separation chamber 120 is injected with a volume of focusing solution that is at least about 0.5 μl or at least about 1 μl, at least about 2 μl, at least about 3 μl, at least about 4 μl, at least about 5 μl, at least about 6 μl, at least about 7 μl, at least about 8 μl, at least about 9 μl, or at least about 10 μl, and, depending upon the dimensions of the separation chamber, up to about up to about 2 μl, up to about 3 μl, up to about 4 μl, up to about 5 μl, up to about 10 μl, up to about 15 μl, up to about 20 μl, or up to about 25 μl.

Focusing

After the focusing solution 10 is prepared and introduced into the separation chamber 120, focusing can be initiated by coupling a first end 121 of the separation chamber 120 to a first buffer reservoir 131 (containing either anolyte or catholyte buffer) and a second end 122 of the separation chamber 120 to a second buffer reservoir 132 (containing either anolyte or catholyte buffer, whichever was not used in the first buffer reservoir), followed by application of an electric field. As used herein, the term "coupling" means that the ends 121, 122 of the separation chamber 120 are in fluid communication with the respective reservoirs 131, 132. The term "fluid communication" means that a fluid can freely pass between the end 121, 122 of the separation chamber 120 and the adjacent reservoir 131, 132. In one embodiment, the separation chamber 120 is coupled to the first 131 and second 132 buffer reservoirs by immersing the respective end 121, 122 of the separation chamber 120 in the solution present in the adjacent reservoir 131, 132.

Under the influence of the electric field, hydrogen ions begin to migrate from the reservoir containing the anolyte toward the reservoir containing the catholyte and hydroxide ions from the catholyte begin to move in the opposite direction, causing the carrier ampholytes to generate a pH gradient. The focusing voltage between about 1 kV to about 50 kV is typically used, for example, at least about 1 kV, at least about 5 kV, at least about 10 kV, at least about 15 kV, at least about 20 kV, and at least about 25 kV and/or up to about 20 kV, up to about 25 kV, up to about 30 kV, up to about 35 kV, up to about 40 kV, up to about 45 kV, or up to about 50 kV. The focusing voltage is generally at least about 300 V/cm, at least about 325 V/cm, at least about 350 V/cm, at least about 375 V/cm and up to about 400 V/cm, up to about 425 V/cm, up to about 450 V/cm, up to about 475 V/cm, up to about 500 V/cm, up to about 550 V/cm, or up to about 600 V/cm.

The focusing voltage is applied until the sample components are focused, i.e., when the sample components are at a pH that corresponds to their respective isoelectric points and migration stop, such that each component is separated into a narrow band located at the pH of its isoelectric point. Once each analyte has migrated to a region where its net charge is neutral, the positions of bands become constant and no longer change with time. In some instances, a voltage drop can be detected once the sample components are focused.

Many factors can affect focusing time. For example, focusing time can be affected by the concentration of salts in the sample. Generally, a higher salt concentration will result in a faster focusing process, since the pH gradient tends to be narrowed by the presence of salts. Alternately, focusing speed may become slower when the concentration of CAs is higher, or voltage is changed. Generally, the focusing time ranges from between about 1 minute and about 120 minutes, for example, from at least about 1 minute, at least about 5 minutes, at least about 10 minutes, at least about 15 minutes, at least about 20 minutes, at least about 25 minutes, at least about 30 minutes and up to about 40 minutes, up to about 45 minutes, up to about 50 minutes, up to about 55 minutes, up to about 60 minutes, up to about 90 minutes, and up to 120 minutes. A voltage gradient can be employed, starting at a lower voltage, and increasing the voltage as time progresses.

Temperature control during cIEF can be important because pIs may be dependent upon temperature. In one embodiment, focusing is performed at a temperature of at least about 0° C., at least about 5° C., at least about 10° C., at least about 15° C., at least about 20° C., and up to about 25° C., up to about 30° C., up to about 35° C., or up to about 40° C.

Mobilization

After the components of the sample solution are focused, they are mobilized out of the separation chamber 120. Generally, mobilization can be accomplished hydrodynamically or chemically. Hydrodynamic mobilization uses either pressure or vacuum (generally between about 0.5 psi and about 50 psi) for mobilization of the focused proteins. Chemical mobilization is carried out by changing the chemical composition of anolyte or catholyte buffer, which results in a shift in the pH gradient which causes migration of the focused sample components. One common chemical mobilization method includes adding a neutral salt such as sodium chloride either to the anolyte and/or catholyte buffer. The sodium ions serve as a non-proton cation in anodic mobilization and chloride functions as a non-hydroxyl anion in cathodic mobilization. In other known chemical mobilization processes, the anodic buffer is replaced with the cathodic buffer (or vice versa). The direction of mobilization (either anodic or cathodic) can be selected depending upon properties of the analyte components, for example, according to the acidic character of the analyte. For cathodic mobilization, the catholyte buffer is replaced with a solution containing another anion. For anodic mobilization, the anolyte buffer is replaced with a solution containing another cation.

In the novel method and system described herein, the mobilization buffer is a sheath flow buffer. In contrast to conventional cEIF-ESI coupling, in which the mobilization buffer for cIEF is a separate solution than the ionization buffer used for ESI, a combined "sheath flow buffer" is used that functions as both the mobilization buffer for cIEF and ionization buffer for ESI. As used herein, the term "sheath flow buffer" refers to a solution that includes a polar organic solvent and an organic acid. Generally, the sheath flow buffer includes between about 25% v/v and about 75% v/v of polar organic solvent, generally at least about 25% v/v, at least about 30% v/v, at least about 35% v/v, at least about 40% v/v, at least about 45% v/v or at least about 50% v/v, and up to about 50% v/v, up to about 55% v/v, up to about 60% v/v, up to about 65% v/v, up to about 70% v/v, or up to about 75% v/v polar organic solvent. As used herein, the term "polar organic solvent" includes both polar protic solvents and polar aprotic solvents. The term "polar protic solvent" refers to a solvent that has a dissociable hydrogen, for example, an alcohol that includes a hydrogen atom bound to an oxygen atom. The term "polar aprotic solvent" refers to a solvent that lacks an acidic hydrogen. Examples of suitable polar protic solvents include aliphatic alcohols including, but not limited to, methanol, ethanol, propanol, butanol, isopropyl alcohol, and combinations thereof. Examples of suitable polar aprotic solvents include acetonitrile. Generally, the sheath flow buffer also includes between about 0.01% v/v and about 1% v/v organic acid, generally at least about 0.01% v/v, at least about 0.05% v/v, or at least about 0.1% v/v and up to about 0.1% v/v, up to about 0.5% v/v or up to about 1.0% v/v organic acid. In one embodiment, the organic acid is a carboxylic acid. Carboxylic acids are organic acids that include at least one carboxyl group and have a general formula of R—COOH. In one embodiment, R— is an alkane. In one embodiment, the carboxylic acid has a pKa between about 3.5 and 5.0. Examples of suitable carboxylic acids include, but are not limited to, formic acid ($HCO_2H$, pKa 3.75), acetic acid ($CH_3COOH$, pKa 4.76), ethanoic acid ($CH_3CO_2H$, pKa 4.7), and propanoic acid ($CH_3CH_2CO_2H$ pKa 4.9).

In one embodiment, the sheath flow buffer includes between about 25% v/v and about 75% v/v of aliphatic alcohol, generally at least about 25% v/v, at least about 30% v/v, at least about 35% v/v, at least about 40% v/v, at least about 45% v/v or at least about 50% v/v, and up to about 50% v/v, up to about 55% v/v, up to about 60% v/v, up to about 65% v/v, up to about 70% v/v, or up to about 75% v/v aliphatic alcohol. In one embodiment, the sheath flow buffer includes between about 25% v/v and about 75% v/v of methanol, generally at least about 25% v/v, at least about 30% v/v, at least about 35% v/v, at least about 40% v/v, at least about 45% v/v or at least about 50% v/v, and up to about 50% v/v, up to about 55% v/v, up to about 60% v/v, up to about 65% v/v, up to about 70% v/v, or up to about 75% v/v methanol. In another embodiment, the sheath flow buffer includes between about between about 25% v/v and about 75% v/v of acetonitrile, generally at least about 25% v/v, at least about 30% v/v, at least about 35% v/v, at least about 40% v/v, at least about 45% v/v or at least about 50% v/v, and up to about 50% v/v, up to about 55% v/v, up to about 60% v/v, up to about 65% v/v, up to about 70% v/v, or up to about 75% v/v acetonitrile. In other embodiments, the sheath flow buffer also includes between about 0.01% v/v and about 1% v/v carboxylic acid, generally at least about 0.01% v/v, at least about 0.05% v/v, or at least about 0.1% v/v and up to about 0.1% v/v, up to about 0.5% v/v or up to about 1.0% v/v carboxylic acid. In a more particular embodiment, the sheath flow buffer includes between about 0.01% v/v and about 1% v/v formic acid, generally at least about 0.01% v/v, at least about 0.05% v/v, or at least about 0.1% v/v and up to about 0.1% v/v, up to about 0.5% v/v or up to about 1.0% v/v formic acid. In a more particular embodiment, the sheath flow buffer includes between about 25% v/v and about 75% v/v of methanol, generally at least about 25% v/v, at least about 30% v/v, at least about 35% v/v, at least about 40% v/v, at least about 45% v/v or at least about 50% v/v, and up to about 50% v/v, up to about 55% v/v, up to about 60% v/v, up to about 65% v/v, up to about 70% v/v, or up to about 75% v/v methanol and between about 0.01% v/v and about 1% v/v formic acid, generally at least about 0.01% v/v, at least about 0.05% v/v, or at least about 0.1% v/v and up to about 0.1% v/v, up to about 0.5% v/v or up to about 1.0% v/v formic acid.

In the novel system described herein, the outlet end 122 of the cIEF separation chamber 120 is coupled online to an input end 211 of the emitter 210 of the electrospray ionization instrument and chemical mobilization of the separated sample components from the separation chamber 120 to the emitter 210 is accomplished using a sheath flow buffer. As used herein, the term "coupled" means that the outlet end 122 of the cIEF separation chamber is in fluid communication with the emitter 210. In one embodiment, the outlet end 122 of the separation chamber 120 is coupled to the emitter 210 by introducing the outlet end 122 of the separation chamber into an inlet end 210 of the emitter 210.

In contrast to conventional cEIF-ESI coupling, in which the eluate from the separation chamber 120 is combined with an ionization solution, the sheath flow buffer (described above) is used as the mobilization solution in the method of the invention. The low flow rate of the sheath flow advantageously decreases the dilution of the sample relative to conventional techniques.

During mobilization, it can be important to maintain an appropriate applied voltage so that the analyte components remain focused and do not diffuse as a result of the mobilization step. At the beginning of mobilization, current initially remains at a low value, similar to that observed at the end of focusing, for example, between about 1 µA and about 10 µA, or at least about 1 µA, at least about 2 µA, at least about 3 µA, at least about 4 µA, at least about 5 µA, and up to about 6 µA, up to about 7 µA, up to about 8 µA, up to about 9 µA, or up to about 10 µA. As mobilization progresses, the current gradually begins to rise as the salt ions enter the capillary. Later in mobilization, when the salt ions are present throughout the column, a rapid rise in current indicates the completion of mobilization, for example, an increase of between about 10 µA and about 20 µA can be observed. In one embodiment, the focused analytes maintain their relative position during mobilization.

During mobilization, the voltage is generally kept between about 1 kV to about 50 kV is used, for example, at least about 1 kV, at least about 5 kV, at least about 10 kV, at least about 15 kV, at least about 20 kV, and at least about 25 kV and/or up to about 20 kV, up to about 25 kV, up to about 30 kV, up to about 35 kV, up to about 40 kV, up to about 45 kV, or up to about 50 kV. The electric field is generally kept at least about 300 V/cm, at least about 325 V/cm, at least about 350 V/cm, at least about 375 V/cm and up to about 400 V/cm, up to about 425 V/cm, up to about 450 V/cm, up to about 475 V/cm, up to about 500 V/cm, up to about 550 V/cm, or up to about 600 V/cm. Mobilization generally takes between about 1 minute and about 30 minutes, for example at least about 1 minute, at least about 5 minutes, at least about 10 minutes, or at least about 15 minutes, and up to about 20 minutes, up to about 20 minutes, up to about 25 minutes or up to about 30 minutes.

Electrospray Ionization (ESI)

Coupling of cEIF and ESI can be performed online or offline. In an online coupling the solution mobilized from the separation chamber 120 is fed directly into an electrospray emitter 210, for example, using a coaxial sheath-flow interface, sheathless interface or a liquid junction interface. Offline methods of coupling include, for example, collecting fractions eluting from the separation chamber 120 to be analyzed later.

In a typical cEIF-ESI coupling, the eluate from the separation chamber is combined with a volatile organic solvent to form an ionization solution 20, which is then introduced into the electrospray emitter 210. See, FIG. 3. Examples of typical volatile organic solvents used to form an ionization solution include methanol and acetonitrile. The ionization solution may also include an ionizing agent, for example, $H^+$, $Na^+$, or $K^+$.

As discussed previously, in contrast to conventional cEIF-ESI coupling, in which the eluate from the separation chamber 120 is combined with an ionization solution, the same sheath flow buffer can be used as both the mobilization solution for cEIF and the ionization solution for ESI.

Figure 3:
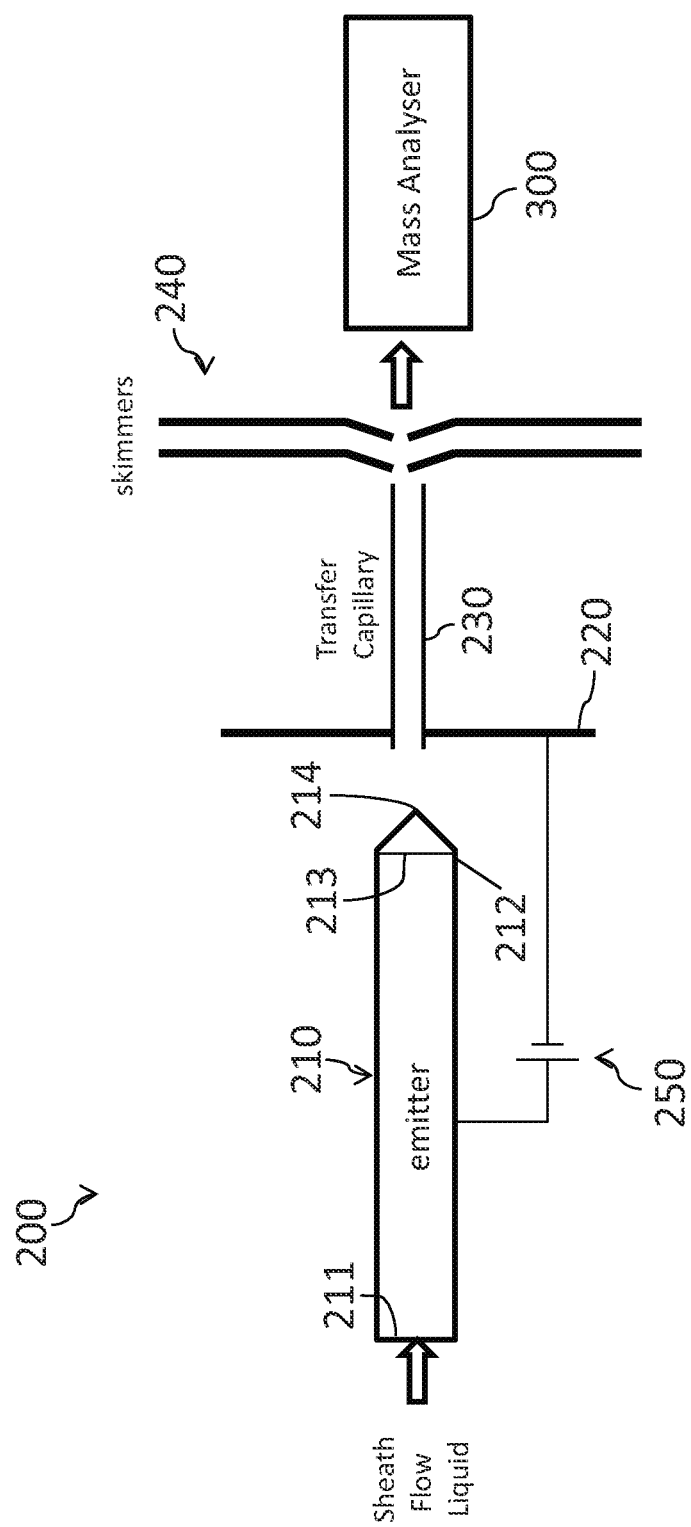
FIG. 3 is a schematic representation of ESI.

As shown in FIG. 3, the electrospray emitter 210 is typically an elongate vessel having an inlet 211 and an outlet 212, wherein the outlet 212 has a small diameter aperture 213 (i.e., an aperture of between about 1 µm and about 10 µm, between about 1 µm and about 5 µm, or between about 2 µm and about 3 µm). A power supply 250 generates an electric potential (typically between about 1 kV and about 10 kV, between about 2 kV to about 6 kV, or between about 3 kV to about 4 kV) is applied between the electrospray emitter 210 and a counter electrode 220. Repulsion between ions in the ionization solution 20 with a surface charge of the same polarity to the charge of the emitter 210 cause ions migrate to the outlet 212 of the emitter 210 and form a cone (called the Taylor cone 214). Once the repulsive forces become greater than the surface tension of the ionization solution 20, a fine aerosol spray is emitted from the outlet 212 of the emitter 210 toward the counter electrode 220. As the droplets traverse the space between the emitter outlet 212 and the counter electrode 220, solvent evaporates. Typically, ionization/evaporation process is performed at atmospheric pressure.

The ionization solution is introduced into the emitter 210 at a flow rate of at least about 0.001 µl/min, at least about 0.005 µl/min, at least about 0.01 µl/min, at least about 0.05 µl/min, at least about 0.1 µl/min, at least about 0.5 µl/min, and up to about 0.1 µl/min, up to about 0.5 µl/min, up to about 1 µl/min, up to about 5 µl/min, up to about 10 µl/min, up to about 50 µl/min, and up to about 100 µl/min.

The electrospray voltage can be between about 1 kv and about 10 kv. The distance between capillary exit and the emitter tip can be between about 1 mm and about 2 mm. The distance between emitter end and MS entrance can be between about 1 mm and about 10 mm, The size of emitter can be between about 2 µm and about 20 µm.

Once the components of the sample solution are separated by cIEF, they can be analyzed by Mass Spectrometry (MS). cIEF can be coupled to MS using electrospray ionization (ESI) as the interface. Electrospray ionization (ESI) is frequently used to ionize thermally labile and high molecular weight compounds such as peptides and other polymers. The invention described herein provides a system for on-line coupling of CIEF with ESI-MS.

Mass Spectrometry

Figure 4:
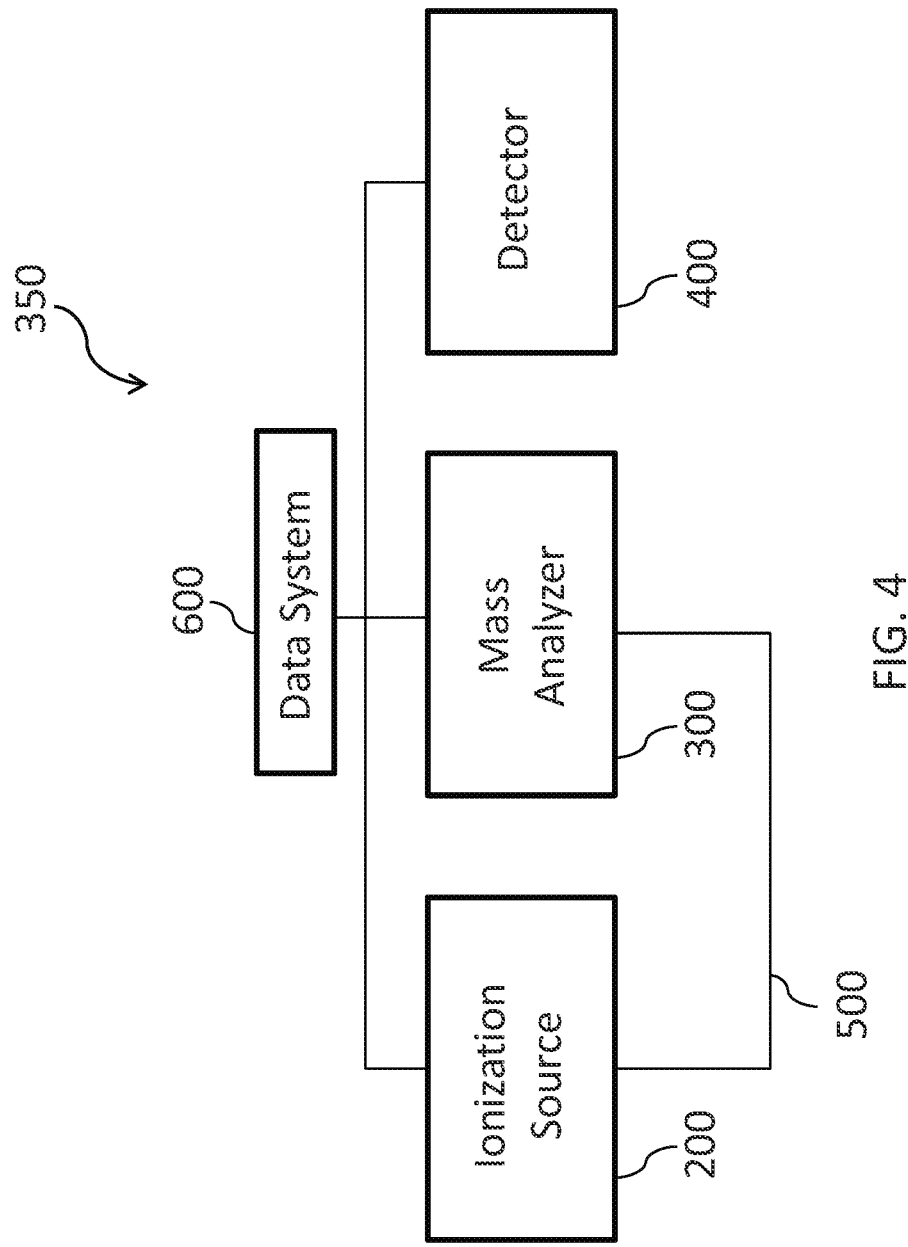
FIG. 4 is a schematic representation of MS.

FIG. 4 is a block diagram that shows the basic components of a mass spectrometer 350. The ion source 200 (ESI, described above) is where neutral sample molecules are ionized. In the mass analyzer 300, the ions are accelerated and separated, either in space or in time, according to their mass to charge ratio (m/z) using an applied electric field.

After the ions are separated, they are detected by a detector 400 and the signal is transferred to a data system 600 for analysis. Detection can be based upon charge or momentum. Older instruments used photographic plates to measure the ion abundance at each mass to charge ratio. Most detectors currently used amplify the ion signal using a collector similar to a photomultiplier tube. These amplifying detectors include: electron multipliers, channeltrons and multichannel plates. A detector is selected for its speed, dynamic range, gain, and geometry. Some detectors are sensitive enough to detect single ions. Data analysis can be performed by database searching, for example to determine the presence of host cell protein (HCP).

Mass spectrometers typically also have a vacuum system 500 to maintain a low pressure to reduce the chance of ions colliding with other molecules in the mass analyzer 300. Collisions can cause the ions to react, neutralize, scatter, or fragment, which can interfere with the mass spectrum. To minimize collisions, experiments are conducted under high vacuum conditions, typically $10^{-2}$ to $10^{-5}$ Pa ($10^{-4}$ to $10^{-7}$ torr) depending upon the geometry of the instrument.

The selection of a mass analyzer depends upon the resolution, mass range, scan rate and detection limits. Each analyzer has very different operating characteristics and the selection of an instrument involves important tradeoffs and can be continuous or pulsed. There are generally five different types of mass spectrometers: (1) magnetic-sector and double-focusing instruments, which use a magnetic field to separate ions as a function of their momentum; (2) transmission quadrupole, which uses a quadrupole field to allow ions of only a single m/z value to pass from the ion source to the detector; (3) quadrupole ion-trap, which uses a quadrupole field to store ions of all m/z values and then destabilize them one m/z value at a time to obtain a mass spectrum; (4) time-of-flight (TOF) mass spectrometer, which accomplishes the separation of accelerated ions of different m/z values as a function of flight time through a field-free region; and (5) Fourier transform ion cyclotron resonance (FTICR) mass spectrometer (sometimes called FTMS), which creates a Fourier transform of an array of resonant frequencies, which corresponds to ions of different m/z values that are stored in a magnetic ion trap. Any of these types of mass spectrometers can be used in connection with the system of the invention.

LTQ-Orbitrap-velos can include a capillary temperature of about 300° C. MS1 Orbitrap analyzer can be at a resolution of 60,000. A parameter for the MS1 Orbitrap analyzer can include a scan range of about 395 m/z to about 1800 m/z. The 12 most intense peaks can be used for MS2 (ion trap), A parameter for the MS1 Orbitrap analyzer can include 35% normalized collision.

As used herein, the term "about" is used to modify, for example, the quantity of an ingredient in a composition, concentration, volume, process temperature, process time, yield, flow rate, pressure, and ranges thereof, employed in describing the invention. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and other similar considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include such equivalents.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of a molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

WORKING EXAMPLES

All reagents were purchased from Sigma Aldrich Co. (St. Louis, Mo., USA) unless otherwise stated.

Example 1

Sample Preparation

Preparation of BSA Digest

A Bovine Serum Albumin (BSA) digest (0.1 mg/mL) was used to evaluate the reproducibility of the cIEF-ESI-MS/MS system. BSA (0.5 mg/mL) was dissolved in 100 mM ammonium bicarbonate (pH 8.0) and denatured at 90° C. for 10 minutes, followed by standard reduction and alkylation process by reduction with dithiothreitol (DTT) (8 mM) at 65° C. for 1 h and alkylation with iodoacetic acid (IAA) (20 mM) at room temperature for 30 min in the dark. Digestion was performed by incubating the proteins for 12 hours at 37° C. with trypsin at a trypsin:protein ratio of 1:30 (w/w). Carboxyl functionalized magnetic microspheres (BioMag®Plus carboxyl, mean diameter ~1.5 µm) were purchased from Bangs Laboratories, Inc. (Fishers, 1N, USA) and activation of carboxyl functionalized magnetic microspheres and trypsin immobilization was performed as described by Li et al., *J. Chromatogr. A* 2011, 1218, 2007-2011.

Preparation of a Three Protein Mixture

A three protein-mixture was also used evaluate the performance of the cIEF-ESI-MS/MS system. The three protein-mixture was prepared with a 50-fold range in concentration and contained 7 µM BSA (0.5 mg/mL), 0.7 µM cytochrome c (0.0095 mg/mL), and 140 nM myoglobin (0.0025 mg/mL). The protein mixture was dissolved in 100 mM ammonium bicarbonate (pH 8.0) and denatured at 90° C. for 10 minutes, followed by standard reduction and alkylation process with dithiothreitol (DTT) and iodoacetic acid (IAA) as described previously. For immobilized trypsin digestion, 30 µL of protein solution was incubated with 200 µg trypsin immobilized beads at 37° C. for 10 minutes. The digests were diluted 1:1 with water deionized by a Nano Pure system from Thermo scientific (Marietta, Ohio, USA) and stored at −20° C. for use.

Depleted Recombinant Human IgG Cell Culture Media

Recombinant human IgG was prepared by MedImmune, Inc using known cell culture processes. The recombinant human IgG was then depleted from test samples using NAb protein A (Thermo Scientific) and protein L (Thermo Scientific) spin columns. Briefly, protein A spin-columns were equilibrated with 1× phosphate buffered saline (PBS; pH 7.2). The IgG sample was diluted with phosphate buffered saline (PBS) and added to a column. Following a ten minute incubation at room temperature with gentle mixing by inversion, the flow-through was collected and immediately added to an equilibrated protein L spin-column. The protein L column was incubated and mixed as described above. The protein L flow-through (depleted culture media) was collected and stored at −80° C. for use.

The flow through fraction obtained from the Protein A/L columns (0.045 mg/mL, 500 μL) (described above) was dried in an Eppendorf concentrator. The dried sample was dissolved in 100 μL 100 mM ammonium bicarbonate ($NH_4HCO_3$) with 1 M urea and denatured at 90° C. for 10 minutes, followed by standard reduction and alkylation process with dithiothreitol (DTT) and iodoacetic acid (IAA), described above. Digestion was performed by incubating 50 μL of denatured proteins with 400 μg immobilized trypsin magnetic beads for 10 minutes at 37° C. The digests were stored at −20° C. for use.

Example 2 cIEF

The instrument used in this example was based on a capillary electrophoresis system described by Wojcik et al., Rapid Commun. Mass Spectrom. 2010, 24, 2554-2560. A commercial linear polyacrylamide (LPA) coated capillary (50 μm i.d., 150 μm o.d., 50 cm long, Polymicro Technologies, Phoenix, Ariz.) was used for the cIEF separation. The anode end of the capillary was placed in formic acid (0.1%, pH 2.5), and the cathode end was placed in 0.3% ammonium hydroxide (pH 11). The capillary was filled with sample prepared in a 0.4% Pharmalyte (3-10) solution (GE Healthcare, Piscataway, N.J.) by purging the solution through the capillary at 2 psi for 3 minutes. The injection volume employed in this experiment is equal to the capillary volume. Focusing voltage was applied at 360 V/cm for 10 minutes.

Example 3

ESI

After focusing, the cathode end of the capillary was inserted into the emitter of the electrospray interface (Wojcik et al., Rapid Commun. Mass. Spectrom. 2010, 24, 2554-2560) and chemical mobilization was performed with a sheath flow buffer such that the sheath flow buffer was used as both the chemical mobilization solution for cIEF and the ionization buffer for electrospray ionization. Three kinds of sheath flow buffer were investigated: 50% methanol and 0.05% acetic acid; 50% methanol and 0.05% formic acid; 50% methanol and 0.1% formic acid. Formic acid (FA) was purchased from Fisher Scientific (Pittsburgh, Pa., USA). The electric field was kept at 330 V/cm during mobilization.

Figure 5:
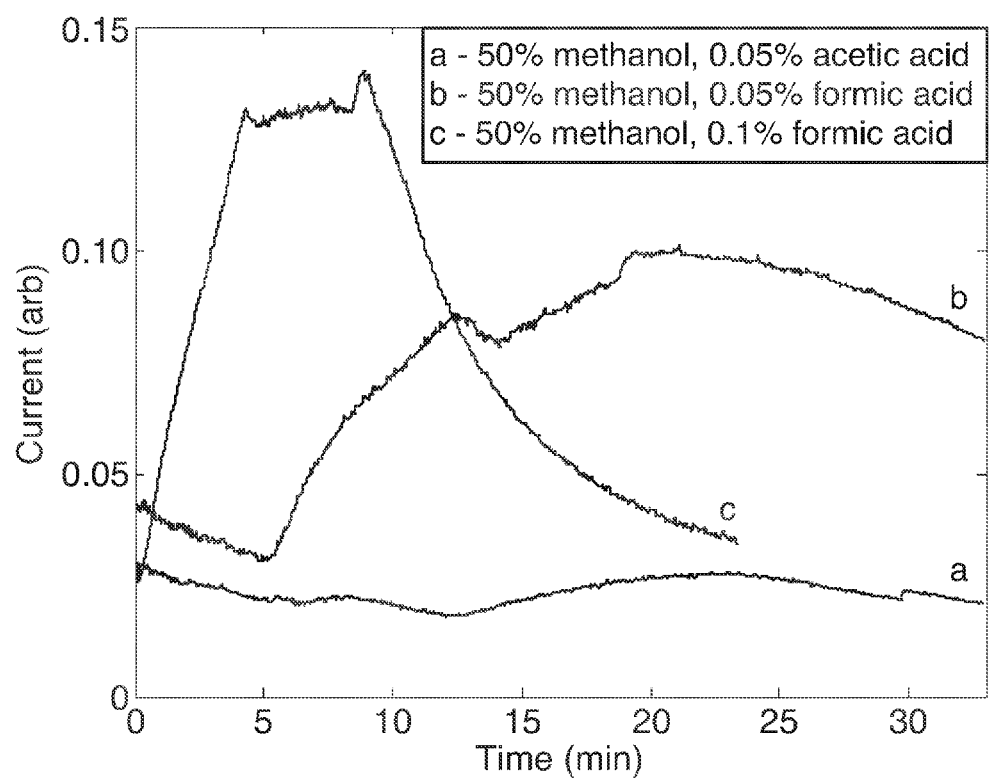
FIG. 5 is a graph showing current profiles for mobilization during cIEF with different sheath flow buffers: (a) 50% methanol and 0.05% acetic acid; (b) 50% methanol and 0.05% formic acid; and (c) 50% methanol and 0.1% formic acid.

FIG. 5 presents the current profiles for the three sheath flow buffers. Curve a shows cIEF chemical mobilization using 0.05% acetic acid in the sheath flow. Curves b and c employed 0.05% formic acid and 0.1% formic acid as a sheath flow buffer, respectively. Current was low and did not change significantly during chemical mobilization with 50% methanol and 0.05% acetic acid.

In contrast, the current increased during chemical mobilization with 50% methanol with 0.05% formic acid and 50% methanol with 0.1% formic acid. The current increased more quickly with 0.1% formic acid than with 0.05% formic acid. It appears that a higher concentration of formic acid speeds mobilization and results in a narrow separation window. In some instances, a short separation window may not be desirable because it can limit the number of tandem mass spectra that can be accumulated during a separation. In order to broaden the separation window and increase the peptide number and protein sequence coverage, 50% methanol with 0.05% formic acid was used as sheath flow in the following experiments.

Example 4

Data Acquisition and Processing

All mass spectrometric experiments were performed using an LTQ-Orbitrap Velos instrument (Thermo Fisher Scientific). Full MS scans were acquired in the Orbitrap mass analyzer over the 395-1900 m/z range with resolution 60,000 (at 400 m/z). The twelve most intense peaks with charge state ≥2 were selected for sequencing and fragmented in the ion trap with normalized collision energy of 35%, activation q=0.25, activation time of 10 microseconds, and one microscan. Peaks selected for fragmentation two or more times within a 45 second window were excluded from selection for an additional 45 seconds.

For standard protein samples, database searching of the raw files was performed in Proteome Discoverer 1.2 with the SEQUEST search engine against ipi.bovin.v3.68.fasta (for BSA and cytochrome c), equine.fasta (for myoglobin). Peptides identified with confidence value as "high" were considered as positive identification.

For the HCP sample, the raw files were first transferred to mgf files. Database searching of mgf files was performed with the MASCOT search engine against SwissProt Rodent. Trans-Proteomic Pipeline (TPP) 4.4 was used to filter the database search results with both peptide probability and protein probability higher than 0.9.

Peptides (25±4) were identified with high confidence producing a sequence coverage of 44±6% in a triplicate analysis. The peptide intensity in the three runs was also analyzed. Table 1 (below) presents the peak intensity of five peptides extracted from spectra obtained in the triplicate runs. The relative standard deviation in peak intensity ranged from 3% to 8%.

TABLE 1

Extracted Peptide Intensity in Triplicate Analysis of BSA Digests

| Peptide m/z | 653.3617 | 751.8099 | 820.4724 | 788.8879 | 847.7277 |
|---|---|---|---|---|---|
| Sequence | HLVDEPQNLIK | EYEATLEEcCAK | KVPQVSTPLVEVSR | LKPDPNTLcDEFK | QEPERNEcFLSH KDDSPDLPK |
| Charge | 2 | 2 | 2 | 2 | 3 |
| Run 1 | $4.69 \times 10^8$ | $1.36 \times 10^8$ | $1.92 \times 10^8$ | $1.11 \times 10^8$ | $4.59 \times 10^7$ |
| Run 2 | $4.99 \times 10^8$ | $1.32 \times 10^8$ | $2.12 \times 10^8$ | $1.16 \times 10^8$ | $4.63 \times 10^7$ |
| Run 3 | $5.02 \times 10^8$ | $1.17 \times 10^8$ | $1.82 \times 10^8$ | $1.19 \times 10^8$ | $4.92 \times 10^7$ |

Table 2 (below) presents the number of identified peptides and the sequence coverage of the three proteins. The analysis consistently identified at least one peptide from the dilute myoglobin sample in the presence of a 50-fold excess of BSA.

TABLE 2

Identification of Three-Protein-Mixture by CIEF-ESI-MS/MS

| | BSA (0.25 µg, 3.5 pmol) | | Cytochrome C (4.8 ng, 350 fmol) | | Myoglobin (1.3 ng, 70 fmol) | |
|---|---|---|---|---|---|---|
| | Number of Peptides | Sequence coverage | Number of Peptides | Sequence Coverage | Number of Peptides | Sequence Coverage |
| Run 1 | 36 | 63.0% | 2 | 17.1% | 2 | 20.3% |
| Run 2 | 38 | 61.6% | 3 | 31.4% | 1 | 20.3% |
| Run 3 | 32 | 61.1% | 3 | 27.6% | 1 | 9.8% |

Figure 6:
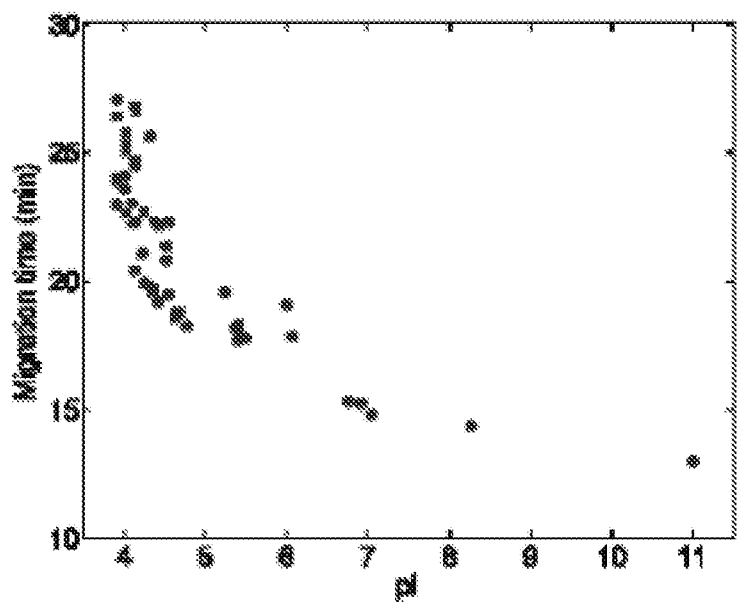
FIG. 6 is a plot showing calculated pI value versus observed migration time of identified peptides from the HCP sample. The pI values of peptide were calculated with TPP and the migration time was obtained from the extracted peptide spectrum.

53 peptides were identified in the depleted antibody sample by tandem mass spectrometry. There is a monotonic but non-linear relationship between the observed migration time and the predicted isoelectric point for these peptides, (see FIG. 6). A plot of pI vs. 1/(Migration time−offset) is linear (r=0.97) for an offset of 11 minutes. This offset reflects the time necessary for the ampholytes to begin to exit the capillary. The inverse relationship reflects the positive chemical mobilization.

After database searching with Mascot and filtering with Trans-Proteomic Pipeline (TPP, v4.4), 37 HCP proteins were identified with probability higher than 0.9 on both the peptide and protein levels after triplicate CIEF-ESI-MS/MS runs. The total analysis time including sample preparation, digestion, and CIEF-ESIMS/MS analysis is about 4 hours.

The invention claimed is:

1. A method for identifying and analyzing one or more components in a sample, the method comprising:
    a. separating one or more components in the sample by capillary isoelectric focusing (cIEF), wherein the sample and an ampholyte buffer are introduced into a separation chamber and focused under an applied voltage;
    b. transferring the separated and focused components directly from the separation chamber to an ionization instrument using a sheath flow solution comprising between about 30% and about 50% polar organic solvent and between about 0.01% and 0.1% organic acid;
    c. ionizing the sample components; and
    d. identifying and analyzing one or more components in the sample by mass spectrometry (MS).

2. The method according to claim 1, wherein the sheath flow solution serves as both a mobilization solution for the separation chamber and an ionization solution for the ionization instrument.

3. The method according to claim 1, wherein the polar organic solvent is selected from polar protic solvents and polar aprotic solvents.

4. The method according to claim 1, wherein separating comprises:
    a. introducing a volume of the sample and an ampholyte buffer into the separation chamber, wherein the separation chamber comprises a capillary; and
    b. focusing the sample and ampholyte buffer in the separation capillary under a focusing voltage of up to about 50 kV.

5. The method according to claim 1, wherein the sample is transferred to the ionization instrument by hydrodynamic injection.

6. The method according to claim 1, wherein the sample comprises a heterogeneous mixture of biomolecules.

7. The method according to claim 1, wherein the sample comprises recombinant protein depleted cell culture.

8. The method according to claim 7, wherein one or more components comprise host cell protein.

9. A system for interfacing capillary isoelectric focusing (cIEF) and mass spectroscopy (MS), comprising:
    a. a cIEF instrument comprising a separation chamber for separating and focusing one or more components in a liquid sample;
    b. a voltage power supply for applying an electrical potential across the separation chamber, wherein the separation chamber contains sample and carrier ampholyte and the electrical potential separates and focuses one or more components in the sample;
    c. a sheath flow solution for transferring one or more separated and focused components directly from the separation chamber of the cIEF instrument to an emitter configured to supply the solution to an electrospray ionization (ESI) instrument, wherein the sheath flow solution comprises between about 30% and about 50% polar organic solvent and between about 0.01% and 0.1% organic acid; and
    d. a MS instrument for analyzing sample analyze.

10. The system according to claim 9, wherein the polar organic solvent is selected from polar protic solvents and polar aprotic solvents.

11. The system according to claim 9, wherein the organic acid is selected from formic acid, acetic acid, ethanoic acid, propanoic acid, benzoic acid, and combinations thereof.

12. The system according to claim 9, wherein the cIEF instrument includes an anode, a cathode, an anolyte reservoir and a catholyte reservoir.

13. The system according to claim 12, comprising an interface coupling device configured to couple an end of the separation chamber to the emitter.

14. The system according to claim 13, wherein the separation chamber comprises a capillary having an anode end, wherein the anode end of the capillary is inserted into an input end of the emitter after focusing of one or more components in the sample to mobilize the focused components.

15. A method for identifying host cell protein (HCP) components in a depleted cell culture sample, the method comprising:
   a. separating one or more HCP components in the sample by capillary isoelectric focusing (cIEF), wherein the sample and an ampholyte buffer are introduced into a separation chamber comprising a fused silica capillary having an inlet end and an outlet end and the one or more HCP components are focused under an applied voltage;
   b. coupling the outlet end of the separation chamber to an inlet end of an electrospray ionization (ESI) instrument;
   c. transferring the separated HCP components from the separation chamber to the emitter of the ESI instrument by introducing a sheath flow solution comprising between about 30% and about 50% polar organic solvent and between about 0.01% and 0.1% organic acid into the inlet end of the separation chamber, wherein the sheath flow solution serves as both a mobilization solution for the separation chamber and an ionization solution for the ionization instrument;
   d. ionizing the sample components; and
   e. identifying and analyzing one or more components in the sample by mass spectrometry (MS).

16. The method according to claim 15, wherein the polar organic solvent is selected from polar protic solvents and polar aprotic solvents.

17. The method according to claim 15, wherein the capillary comprises a polymeric coating.

18. The method according to claim 15, further comprising a step of digesting one or more components in the sample prior to introducing the sample into the separation capillary.

19. The method according to claim 18, wherein the sample is diluted with water after digestion, combined with a carrier ampholyte and introduced into the separation chamber.

20. The method according to claim 15, wherein one or more components comprise protein and the method includes denaturing proteins in the sample prior to introduction of sample into the separation chamber.

\* \* \* \* \*